(12) United States Patent
Jevons et al.

(10) Patent No.: US 7,451,047 B2
(45) Date of Patent: *Nov. 11, 2008

(54) SYSTEM AND METHOD FOR PROGRAMATIC ACCESS TO BIOLOGICAL PROBE ARRAY DATA

(75) Inventors: Luis Jevons, Sunnyvale, CA (US); Derek Bernhart, Lafayete Hill, PA (US); Nga Yu Cheung, San Jose, CA (US); Conrad Sheppy, Redwood City, CA (US)

(73) Assignee: Affymetrix, Inc., Santa Clara, CA (US)

( * ) Notice: Subject to any disclaimer, the term of this patent is extended or adjusted under 35 U.S.C. 154(b) by 215 days.

This patent is subject to a terminal disclaimer.

(21) Appl. No.: 11/215,900

(22) Filed: Aug. 31, 2005

(65) Prior Publication Data

US 2006/0074563 A1     Apr. 6, 2006

Related U.S. Application Data

(63) Continuation of application No. 10/370,442, filed on Feb. 19, 2003, now Pat. No. 6,954,699, and a continuation-in-part of application No. 09/683,912, filed on Mar. 1, 2002, now abandoned.

(60) Provisional application No. 60/442,684, filed on Jan. 24, 2003, provisional application No. 60/369,196, filed on Apr. 1, 2002, provisional application No. 60/358,119, filed on Feb. 19, 2002.

(51) Int. Cl.
   *G06F 17/00*   (2006.01)

(52) U.S. Cl. ............................... 702/19; 435/6; 702/20
(58) Field of Classification Search ....................... None
    See application file for complete search history.

(56) References Cited

U.S. PATENT DOCUMENTS 6,804,679 B2 * 10/2004 Jevons et al. ................. 707/102
6,954,699 B2 * 10/2005 Jevons et al. .................. 702/19

OTHER PUBLICATIONS

Lion Bioscience, Product Info, http://www.lionbioscience.com/solutions/arrayscout/product-info 3 pages, 2002.
Lion Bioscience, Release Notes for arraySCOUT; http://www.unikoeln.de/RRZK/software/fachspezifisch/Biologie-Genetik/Software ReleaseNotes-aS2.0.html; 2 pages; version 2.0, 2001.
Lion Bioscience, Press Releases 2001, Life Science Informatics & Discovery; http://www.lionbioscience.com/press/release/2001/showReleases?ID=178; 2 pages.
Cimarron Software, Inc.—Products; 2 pages; Copyright 2000 Cimarron Software, Inc; http://www.cimsoft.com/products.html, 2000.
Alon et al., Proc. Natl. Acad. Sci. USA. 96 : 6745 (1996) ; 5 Pages.

* cited by examiner

*Primary Examiner*—James Martinell
(74) *Attorney, Agent, or Firm*—Leticia R. Block

(57) ABSTRACT

An applications programming interface is described that includes code libraries that enable transfer of pixel data, intermediate results data, or both, from a data structure or data file directly or indirectly to a user-provided application. The pixel data and intermediate results data may include data from biological experiments related probe arrays.

30 Claims, 9 Drawing Sheets

SYSTEM AND METHOD FOR PROGRAMATIC ACCESS TO BIOLOGICAL PROBE ARRAY DATA

RELATED APPLICATIONS

This application is a continuation of and claims priority from U.S. patent application Ser. No. 10/370,442, entitled "System and Method for Programmatic Access to Biological Probe Array Data", filed Feb. 19, 2003, which claims priority from U.S. Provisional Patent Applications Ser. Nos. 60/442,684, titled "System, Method and Computer Software for Instrument Control and Data Acquisition, Analysis, Management and Storage", filed Jan. 24, 2003; 60/369,196, titled "A System and Method for Programmatic Access to Data Stored within Image Processing Software Systems", filed Apr. 1, 2002; and 60/358,119, titled "GeneChip Data Access Components for Programmatic Access to Data Stored Within the GeneChip Software Systems", filed Feb. 19, 2002. This application is also a continuation in part of U.S. patent application Ser. No. 09/683,912, titled "System and Method for Management of Microarray and Laboratory Information", filed Mar. 1, 2002. Each of the preceding patents is hereby incorporated herein by reference in its entirety for all purposes.

COPYRIGHT NOTICE

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND

The present invention is related to systems, methods, and products for accessing and managing biological data generated by scanning arrays of biological materials.

Synthesized nucleic acid probe arrays, such as Affymetrix GeneChip® probe arrays, and spotted probe arrays, have been used to generate unprecedented amounts of information about biological systems. For example, the GeneChip® Human Genome U133 Set (HG-U133A and HG-U133B) available from Affymetrix, Inc. of Santa Clara, Calif., is comprised of two microarrays containing over 1,000,000 unique oligonucleotide features covering more than 39,000 transcript variants that represent more than 33,000 human genes. Analysis of expression data from such microarrays may lead to the development of new drugs and new diagnostic tools.

SUMMARY OF THE INVENTION

There is a demand among users of probe arrays and others for methods and systems for organizing, accessing and analyzing the vast amount of information collected using nucleic acid probe arrays or using other types of probe arrays. These methods may include the use of software applications and related hardware that implement so-called "laboratory information management systems" (hereafter, LIMS). Also, there is a need to integrate users' data generation and/or management methods and systems with LIMS. For example, a user may have unique and/or proprietary systems, methods, and/or software developed by the user or by a third party (hereafter sometimes referred to for convenience as "user-provided application") used to generate, store, and/or process information about experiments with probe arrays. The user may wish to provide this information directly to LIMS without the need for intervening operations. As another, non-limiting example, a user may have user-provided application for mining, analyzing, visualizing, or otherwise processing data managed by the LIMS. The user may wish to access this data directly from LIMS and process it in the user's proprietary ways.

Systems, methods, and computer program products are described herein to address these and other needs. Reference will now be made in detail to illustrative, non-limiting, embodiments. Various other alternatives, modifications and equivalents are possible. As but one of many examples, while certain systems, methods, and computer software products are described using exemplary embodiments for analyzing data from experiments that employ GeneChip® probe arrays from Affymetrix, Inc., or spotted arrays made with 417™ or 427™ Arrayers from Affymetrix, these systems, methods, and products may be applied with respect to other probe arrays and parallel biological assays.

In some embodiments, a method for analyzing molecules by enabling a user-provided application to access data structures is described that includes the steps of providing an applications programming interface having code libraries, and employing the code libraries to enable transfer of pixel data, intermediate results data, or both, directly or indirectly from the data structures to the user-provided application, wherein the pixel data is based on an emission signal having emission values. The emission signal being responsive to an excitation beam directed to probe locations on a probe array, with each probe location having probe molecules.

In some implementations the pixel data and the intermediate results data includes data from biological experiments. The probe molecules may also include nucleic acids including synthesized nucleic acids, and peptides or polysaccharides. The probe array may also include a spotted array.

In some implementations, the method may include enabling target molecules to interact with probe molecules. The target molecules may include biological materials such as cells; proteins, genes, EST's, or other DNA sequences, ligand, receptor, peptide, or nucleic acid.

Additionally, in some implementations the code libraries include an object type library, and executable code callable from the user-provided application. The applications programming interface may hide the format of the data files, and may be downloadable from a remote source. Also, the code libraries may enable export of data elements to a standardized format that includes a MAGE-ML format.

In some embodiments, the method may further include storing the pixel data, the intermediate results data, or both, in one or more data files, and enabling the user-provided application access to the data files. The user-provided application includes an applications programming interface that employs code libraries to enable transfer data elements directly or indirectly from the data files to the user-provided application.

In some implementations the data files may include a .DAT-type file, a .CEL-type file, a .CHP-type file, and a probe array data file that could include a .CDF-type file. The data elements may include probe set data, quality control data, probe array name, x, y coordinate data, probe array type data, sample data, hybridization data, scan data, corner feature data, intensity data by probe position, intensity data by line, algorithm parameter data, probe intensity data by index, probe intensity data by position, probe intensity data by index and position, standard deviation data, pixel data, outlier data, masked feature data, background quality control data, header data, probe set data including data by index or all probe sets, statistical results, empirical results, probe pair data including intensity by x, y coordinates, perfect match probes, mismatch probes, background intensity, or quality control data.

Also described is an embodiment of an applications programming interface that includes code libraries that enable transfer of pixel data, intermediate results data, or both, from a data structure directly or indirectly to a user-provided application. The pixel data and intermediate results data may include data from biological experiments that are related to probe arrays.

In some implementations, the code libraries include an object type library and executable code callable from the user-provided application.

In some embodiments, the applications programming interface may further include server executables that interface between the executable code and the data structure. The server executables may include a COM server.

Also, in some implementations, the number of biological experiments is more than one, and the code libraries further enable batch transfer of the pixel data, the intermediate results data, or both, from the more than one biological experiments. The biological experiments may include experiments using a synthesized array or a spotted array, or alternatively using a synthesized array and a spotted array. The data structure may conform to a publish database schema that could include the AADM schema, and that could be included in a laboratory information management system.

In some implementations, the user-provided application may include a data-mining tool, an image-processing tool, or a data-processing tool. Additionally, the user-provided application could include a data-processing tool that may further include the functions of determining degrees of hybridization, determining absolute expression of genes or EST's, determining differential expression over two or more experiments of genes or EST's, making genotype comparisons, detecting polymorphisms, or detecting mutations.

Additionally, in some implementations, the code libraries may enable the use of high or low level programming languages including Java, C++, Visual C ++, Visual Basic, ASP (Active Server Pages). The code libraries may also enable transfer of pixel data, intermediate results data, or both, from at least one data element from one or more data files directly or indirectly to a user-provided application.

The above implementations are not necessarily inclusive or exclusive of each other and may be combined in any manner that is non-conflicting and otherwise possible, whether they be presented in association with a same, or a different, aspect or implementation. The description of one implementation is not intended to be limiting with respect to other implementations. Also, any one or more function, step, operation, or technique described elsewhere in this specification may, in alternative implementations, be combined with any one or more function, step, operation, or technique described in the summary. Thus, the above implementations are illustrative rather than limiting.

BRIEF DESCRIPTION OF THE DRAWINGS

The above and further advantages will be more clearly appreciated from the following detailed description when taken in conjunction with the accompanying drawings. In the drawings, like reference numerals indicate like structures or method steps and the leftmost digit of a reference numeral indicates the number of the figure in which the referenced element first appears (for example, the element 120 appears first in FIG. 1).

DETAILED DESCRIPTION

Figure 1:
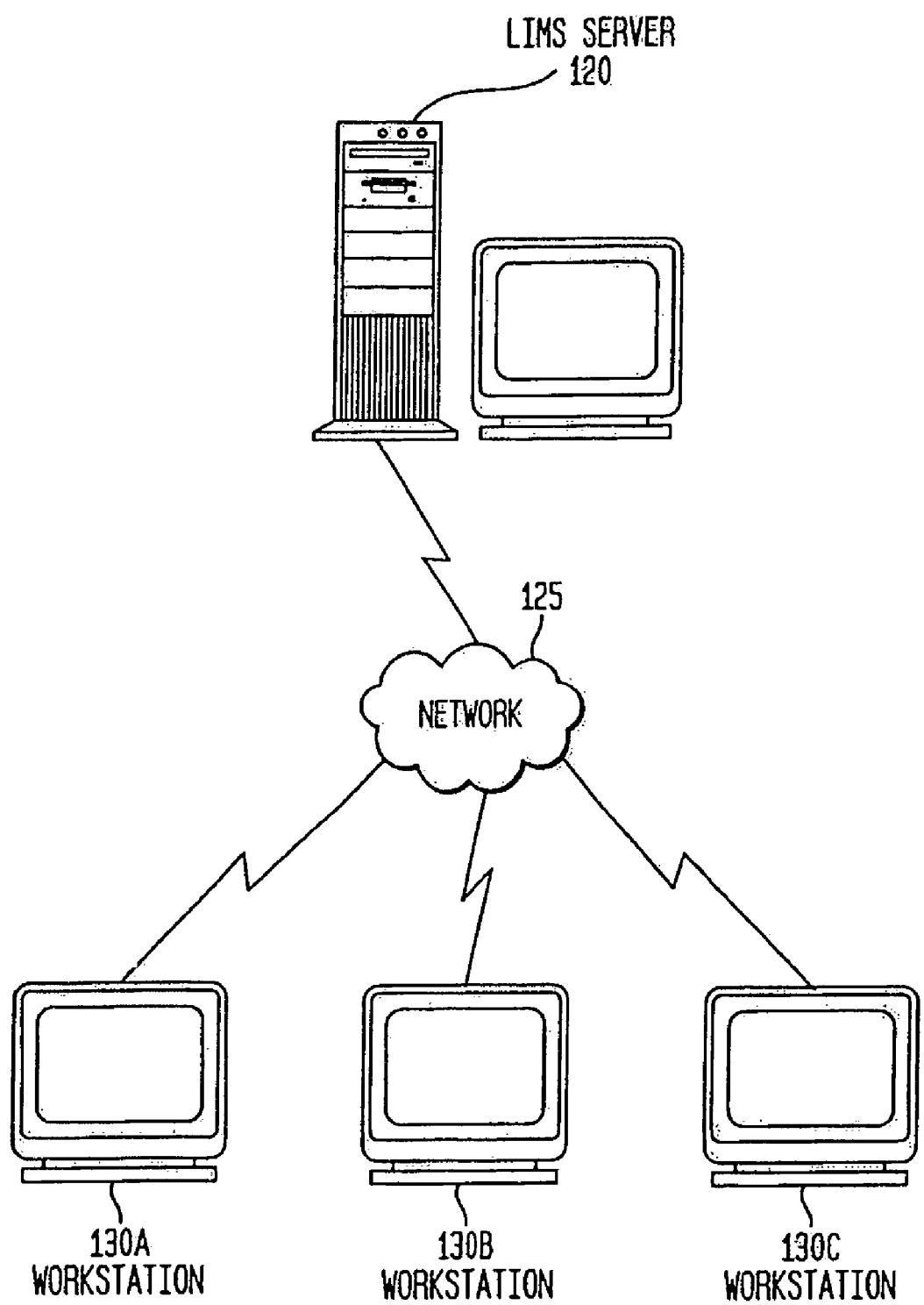
FIG. 1 is a functional block diagram of one embodiment of a computer network system including user workstations coupled to a server suitable for execution of LIMS and LIMS SDK software applications in accordance with one embodiment of the present invention.
Figure 2:
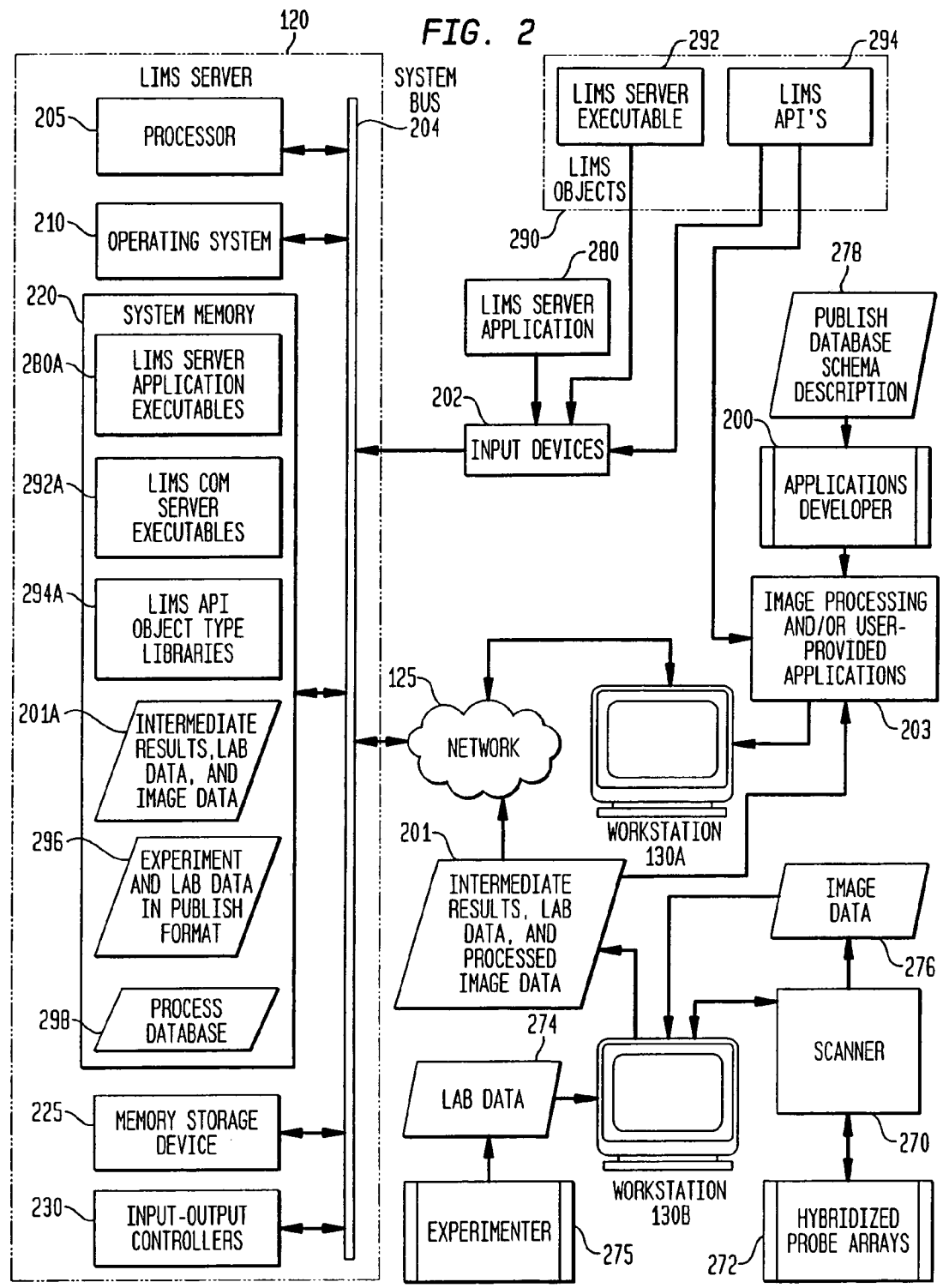
FIG. 2 is a functional block diagram of the LIMS server of FIG. 1 including illustrative embodiments of LIMS and LIMS SDK applications, as well as connections to user workstations.

The present invention may be embodied as a method; data processing, management, and/or analysis system; software program product or products; networked computer and scanning system; other computer and/or scanning systems; or any combination thereof. Illustrative embodiments are now described with reference to the computer network system shown in FIGS. 1 through 4. The operations of this computer network system, and of the LIMS and LIMS-SDK software applications that are executed on computers of this system such as workstation 130A, 130B, or 130C of FIG. 1, are illustrated in the context of the processing of data generated from hybridized probe arrays, such as arrays 272 of FIG. 2. This data processing includes the scanning of arrays 272 by scanner 270 and the processing of the resulting information (and other data) by software executing on representative workstation 130B. Further data processing is carried out in the illustrated embodiment by LIMS server 120. Each of these elements of FIG. 2 are now described in turn.

Hybridized Probe Arrays 272: Various techniques and technologies may be used for synthesizing dense arrays of biological materials on or in a substrate or support. For example, Affymetrix® GeneChip® arrays are synthesized in accordance with techniques sometimes referred to as VLSPS™ (Very Large Scale Immobilized Polymer Synthesis) technologies. Some aspects of VLSIPS™ and other microarray manufacturing technologies are described in U.S. Pat. Nos. 5,424,186; 5,143,854; 5,445,934; 5,744,305; 5,831, 070; 5,837,832; 6,022,963; 6,083,697; 6,291,183; 6,309,831; and 6,310,189, all of which are hereby incorporated by reference in their entireties for all purposes. The probes of these arrays in some implementations consist of nucleic acids that are synthesized by methods including the steps of activating regions of a substrate and then contacting the substrate with a selected monomer solution. As used herein, nucleic acids may include any polymer or oligomer of nucleosides or nucleotides (polynucleotides or oligonucleotides) that include pyrimidine and/or purine bases, preferably cytosine, thymine, and uracil, and adenine and guanine, respectively. Nucleic acids may include any deoxyribonucleotide, ribonucleotide, and/or peptide nucleic acid component, and/or any chemical variants thereof such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. Probes of other biological materials, such as peptides or polysaccharides as non-limiting examples, may also be formed. For more details regarding possible implementations, see U.S. Pat. No. 6,156,501, which is hereby incorporated by reference herein in its entirety for all purposes.

A system and method for efficiently synthesizing probe arrays using masks is described in U.S. patent application Ser. No. 09/824,931, filed Apr. 3, 2001, that is hereby incorporated by reference herein in its entirety for all purposes. A system and method for a rapid and flexible microarray manufacturing and online ordering system is described in U.S. Provisional Patent Application, Ser. No. 60/265,103, filed Jan. 29, 2001, that also is hereby incorporated herein by reference in its entirety for all purposes. Systems and methods for optical photolithography without masks are described in U.S. Pat. No. 6,271,957 and in U.S. patent application Ser. No. 09/683,374 filed Dec. 19, 2001, both of which are hereby incorporated by reference herein in their entireties for all purposes.

The probes of synthesized probe arrays typically are used in conjunction with biological target molecules of interest, such as cells, proteins, genes or EST's, other DNA sequences, or other biological elements. More specifically, the biological molecule of interest may be a ligand, receptor, peptide, nucleic acid (oligonucleotide or polynucleotide of RNA or DNA), or any other of the biological molecules listed in U.S. Pat. No. 5,445,934 (incorporated by reference above) at column 5, line 66 to column 7, line 51. For example, if transcripts of genes are the interest of an experiment, the target molecules would be the transcripts. Other examples include protein fragments, small molecules, etc. Target nucleic acid refers to a nucleic acid (often derived from a biological sample) of interest. Frequently, a target molecule is detected using one or more probes. As used herein, a probe is a molecule for detecting a target molecule. A probe may be any of the molecules in the same classes as the target referred to above. As non-limiting examples, a probe may refer to a nucleic acid, such as an oligonucleotide, capable of binding to a target nucleic acid of complementary sequence through one or more types of chemical bonds, usually through complementary base pairing, usually through hydrogen bond formation. As noted above, a probe may include natural (i.e. A, G, U, C, or T) or modified bases (7-deazaguanosine, inosine, etc.). In addition, the bases in probes may be joined by a linkage other than a phosphodiester bond, so long as the bond does not interfere with hybridization. Thus, probes may be peptide nucleic acids in which the constituent bases are joined by peptide bonds rather than phosphodiester linkages. Other examples of probes include antibodies used to detect peptides or other molecules, any ligands for detecting its binding partners. When referring to targets or probes as nucleic acids, it should be understood that these are illustrative embodiments that are not to limit the invention in any way.

The samples or target molecules of interest (hereafter, simply targets) are processed so that, typically, they are spatially associated with certain probes in the probe array. For example, one or more tagged targets are distributed over the probe array. In accordance with some implementations, some targets hybridize with probes and remain at the probe locations, while non-hybridized targets are washed away. These hybridized targets, with their tags or labels, are thus spatially associated with the probes. The hybridized probe and target may sometimes be referred to as a probe-target pair. Detection of these pairs can serve a variety of purposes, such as to determine whether a target nucleic acid has a nucleotide sequence identical to or different from a specific reference sequence. See, for example, U.S. Pat. No. 5,837,832, referred to and incorporated above. Other uses include gene expression monitoring and evaluation (see, e.g., U.S. Pat. No. 5,800,992 to Fodor, et al.; U.S. Pat. No. 6,040,138 to Lockhart, et al.; and International App. No. PCT/US98/15151, published as WO99/05323, to Balaban, et al.), genotyping (U.S. Pat. No. 5,856,092 to Dale, et al.), or other detection of nucleic acids. The '992, '138, and '092 patents, and publication WO99/05323, are incorporated by reference herein in their entireties for all purposes.

Other techniques exist for depositing probes on a substrate or support. For example, "spotted arrays" are commercially fabricated, typically on microscope slides. These arrays consist of liquid spots containing biological material of potentially varying compositions and concentrations. For instance, a spot in the array may include a few strands of short oligonucleotides in a water solution, or it may include a high concentration of long strands of complex proteins. The Affymetrix® 417™ Arrayer and 427™ Arrayer are devices that deposit densely packed arrays of biological materials on microscope slides in accordance with these techniques. Aspects of these, and other, spot arrayers are described in U.S. Pat. Nos. 6,040,193 and 6,136,269; in U.S. patent application Ser. No. 09/683,298; and in PCT Application No. PCT/US99/00730 (International Publication Number WO 99/36760), all of which are hereby incorporated by reference in their entireties for all purposes. Other techniques for generating spotted arrays also exist. For example, U.S. Pat. No. 6,040,193 to Winkler, et al. is directed to processes for dispensing drops to generate spotted arrays. The '193 patent, and U.S. Pat. No. 5,885,837 to Winkler, also describe the use of micro-channels or micro-grooves on a substrate, or on a block placed on a substrate, to synthesize arrays of biological materials. These patents further describe separating reactive regions of a substrate from each other by inert regions and spotting on the reactive regions. The '193 and '837 patents are hereby incorporated by reference in their entireties. Another technique is based on ejecting jets of biological material to form a spotted array. Other implementations of the jetting technique may use devices such as syringes or piezo electric pumps to propel the biological material. Various other techniques exist for synthesizing, depositing, or positioning biological material onto or within a substrate.

To ensure proper interpretation of the term "probe" as used herein, it is noted that contradictory conventions exist in the relevant literature. The word "probe" is used in some contexts to refer not to the biological material that is synthesized on a substrate or deposited on a slide, as described above, but to what has been referred to herein as the "target." To avoid confusion, the term "probe" is used herein to refer to probes such as those synthesized according to the VLSIPS™ technology; the biological materials deposited so as to create spotted arrays; and materials synthesized, deposited, or positioned to form arrays according to other current or future technologies. Thus, microarrays formed in accordance with any of these technologies may be referred to generally and collectively hereafter for convenience as "probe arrays." Moreover, the term "probe" is not limited to probes immobilized in array format. Rather, the functions and methods described herein may also be employed with respect to other parallel assay devices. For example, these functions and methods may be applied with respect to probe-set identifiers that identify probes immobilized on or in beads, optical fibers, or other substrates or media.

Probes typically are able to detect the expression of corresponding genes or EST's by detecting the presence or abundance of mRNA transcripts present in the target. This detection may, in turn, be accomplished by detecting labeled cRNA that is derived from cDNA derived from the mRNA in the target. In general, a group of probes, sometimes referred to as a probe set, contains sub-sequences in unique regions of the transcripts and does not correspond to a full gene sequence. Further details regarding the design and use of probes are provided in U.S. Pat. No. 6,188,783; in PCT Application Ser. No. PCT/US 01/02316, filed Jan. 24, 2001; and in U.S. patent application Ser. No. 09/721,042, filed on Nov. 21, 2000, Ser. No. 09/718,295, filed on Nov. 21, 2000, Ser. No. 09/745,965, filed on Dec. 21, 2000, and Ser. No. 09/764,324, filed on Jan. 16, 2001, all of which patents and patent applications are hereby incorporated herein by reference in their entireties for all purposes.

Scanner 270: Labeled targets in hybridized probe arrays 272 may be detected using various commercial devices, sometimes referred to as scanners. An illustrative device is shown in FIG. 2 as scanner 270. Scanners image the targets by detecting fluorescent or other emissions from the labels, or by detecting transmitted, reflected, or scattered radiation. A typical scheme employs optical and other elements to provide excitation light and to selectively collect the emissions. Also generally included are various light-detector systems employing photodiodes, charge-coupled devices, photomultiplier tubes, or similar devices to register the collected emissions. For example, a scanning system for use with a fluorescent label is described in U.S. Pat. No. 5,143,854, incorporated by reference above. Other scanners or scanning systems are described in U.S. Pat. Nos. 5,578,832; 5,631,734; 5,834,758; 5,936,324; 5,981,956; 6,025,601; 6,141,096; 6,185,030; and 6,201,639; in PCT Application PCT/US99/06097 (published as WO99/47964); in U.S. patent application Ser. Nos. 09/682,837 filed Oct. 23, 2001, 09/683,216 filed Dec. 3, 2001, and 09/683,217 filed Dec. 3, 2001, 09/683,219 filed Dec. 3, 2001; and in U.S. Provisional Patent Application Ser. Nos. 60/364,731 filed Mar. 15, 2002, 60/396,457 filed Jul. 17, 2002, and 60/435,178 filed Dec. 19, 2002, each of which patent and patent application is hereby incorporated by reference in its entirety for all purposes.

Scanner 270 provides image data 276 representing the intensities (and possibly other characteristics, such as color) of the detected emissions, as well as the locations on the substrate where the emissions were detected. Typically, image data 276 includes intensity and location information corresponding to elemental sub-areas of the scanned substrate. The term "elemental" in this context means that the intensities, and/or other characteristics, of the emissions from this area each are represented by a single value. When displayed as an image for viewing or processing, elemental picture elements, or pixels, often represent this information. Thus, for example, a pixel may have a single value representing the intensity of the elemental sub-area of the substrate from which the emissions were scanned. The pixel may also have another value representing another characteristic, such as color. Two examples of image data are data files in the form *.dat or *.tif as generated respectively by Affymetrix® Microarray Suite based on images scanned from GeneChip® arrays, and by Affymetrix® Jaguar™ software based on images scanned from spotted arrays.

Figure 3:
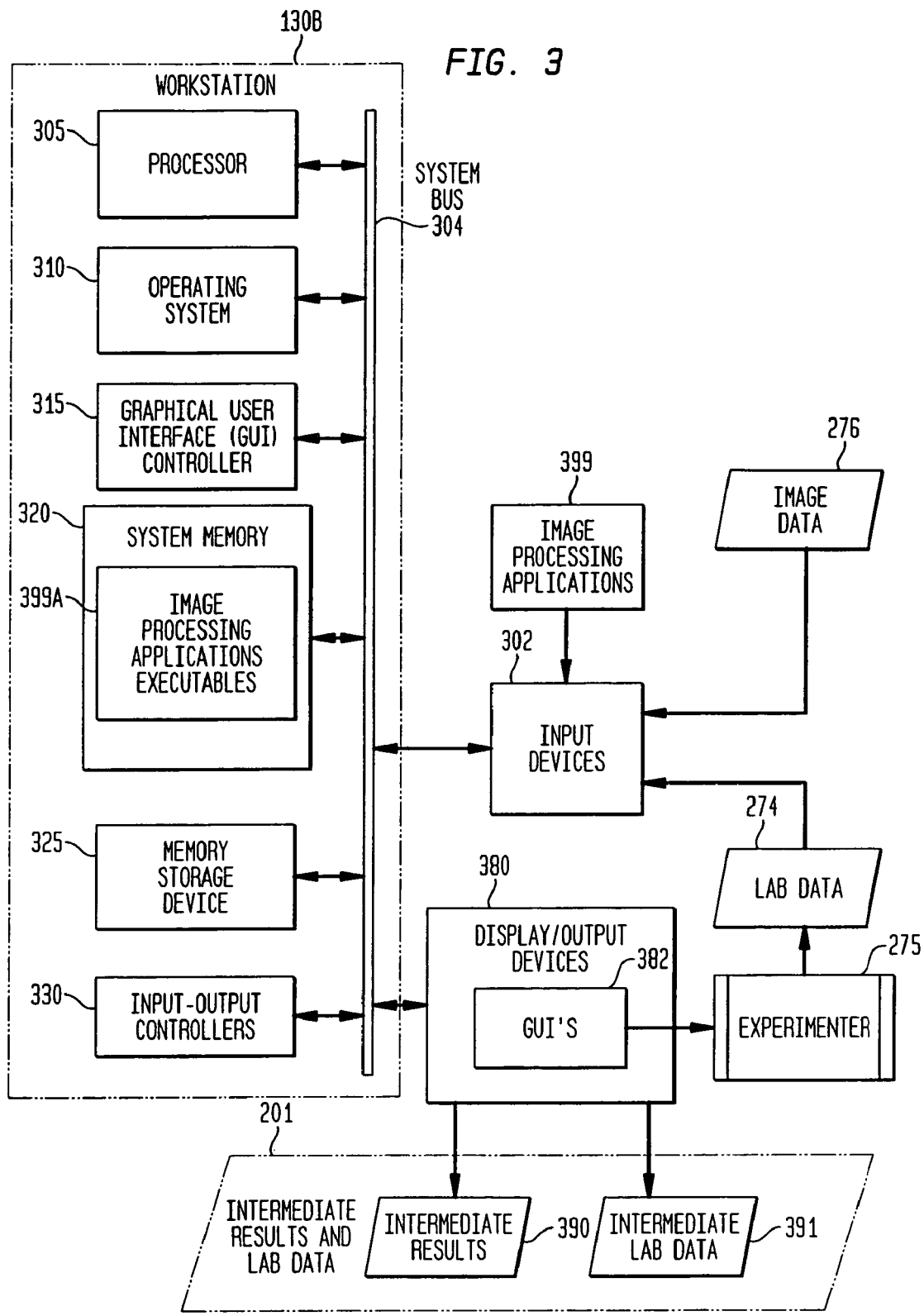
FIG. 3 is a functional block diagram of one embodiment of a user workstation of FIG. 1 suitable for execution of image processing applications.
Figure 4:
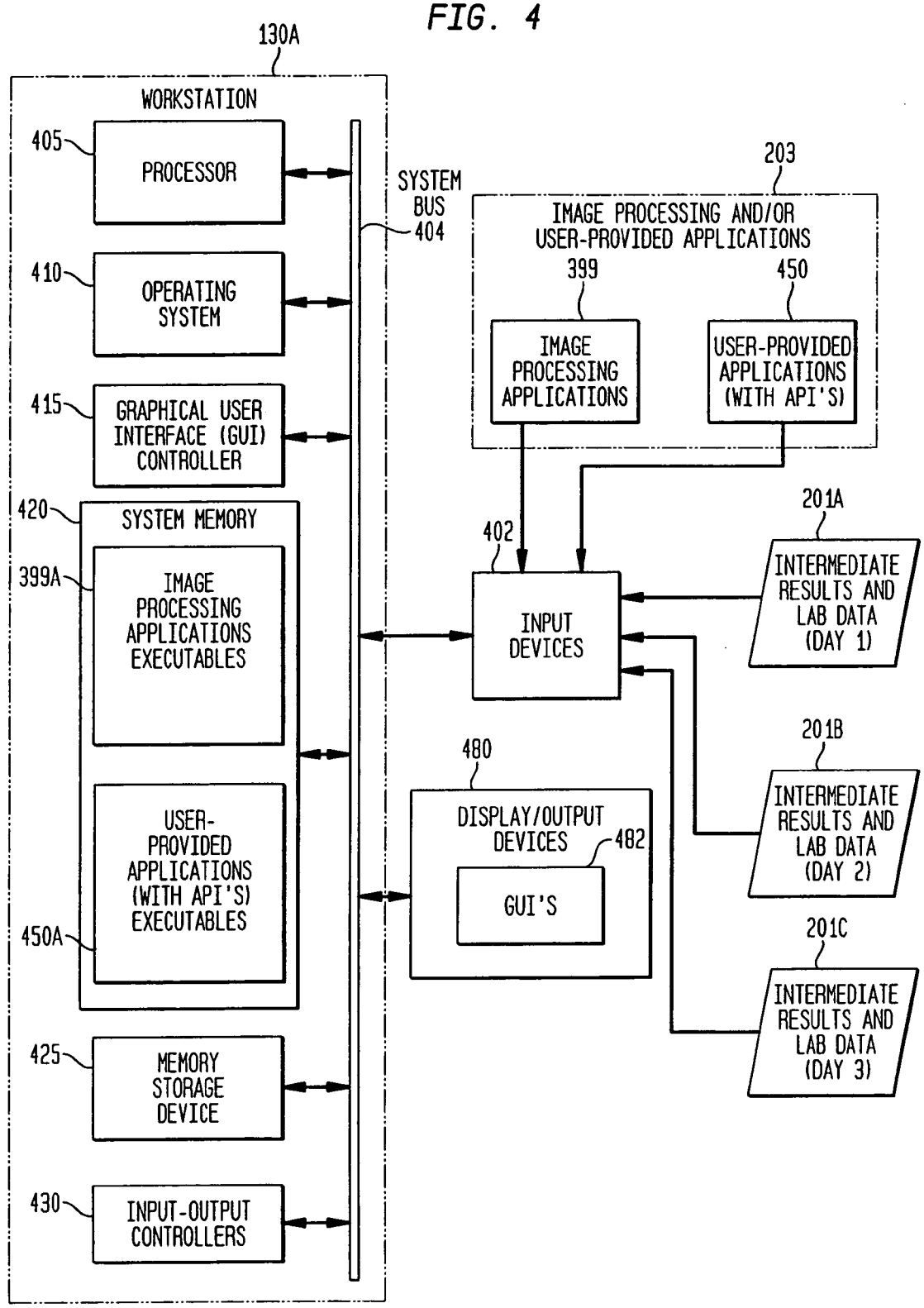
FIG. 4 is a functional block diagram of one embodiment of a user workstation of FIG. 1 suitable for execution of user-provided applications including applications programming interfaces.
Figure 5A:
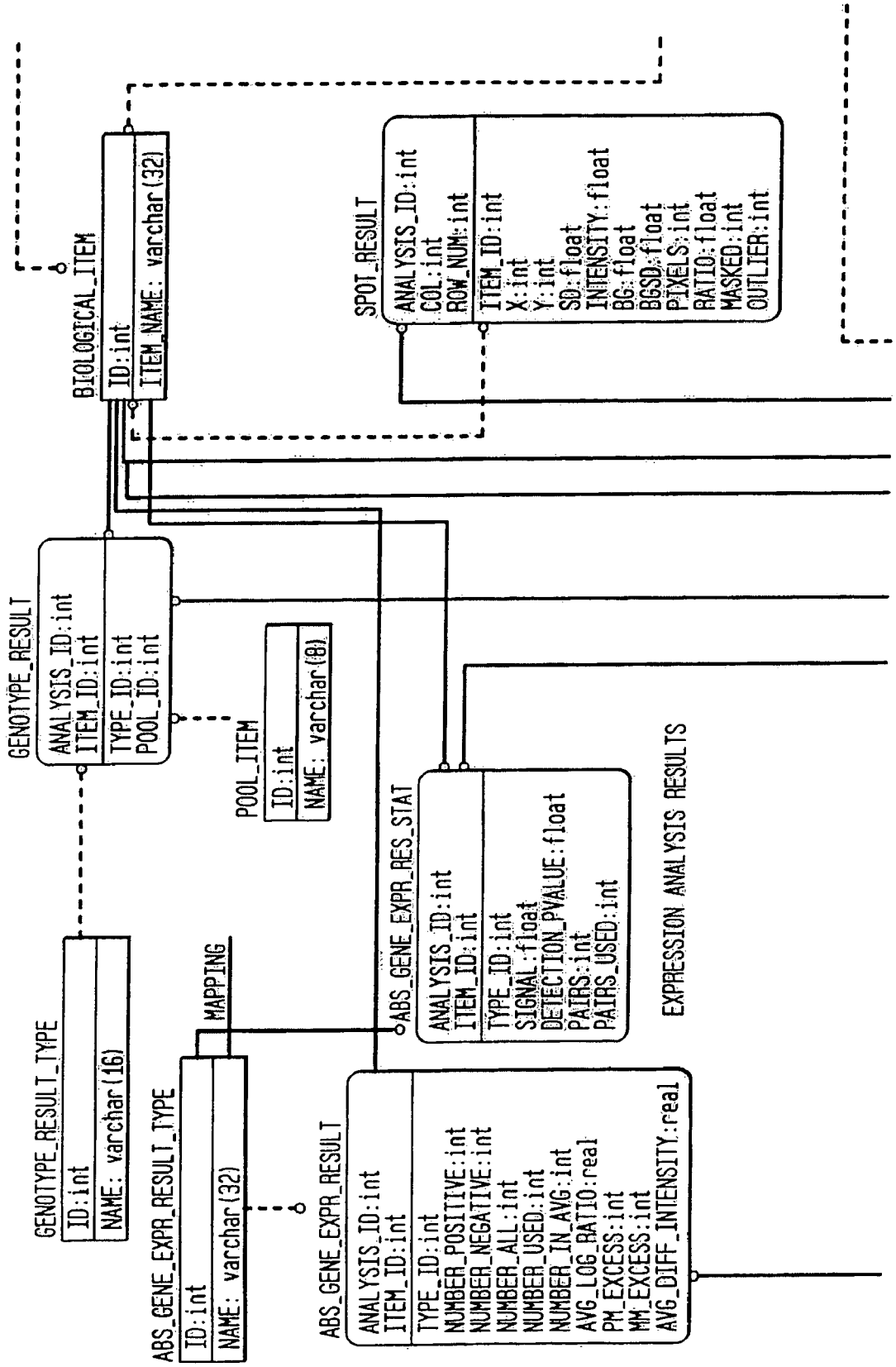
FIGS. 5A-5D are graphical representations of an illustrative database schema for storing information related to experiments with probe arrays.
Figure 5B:
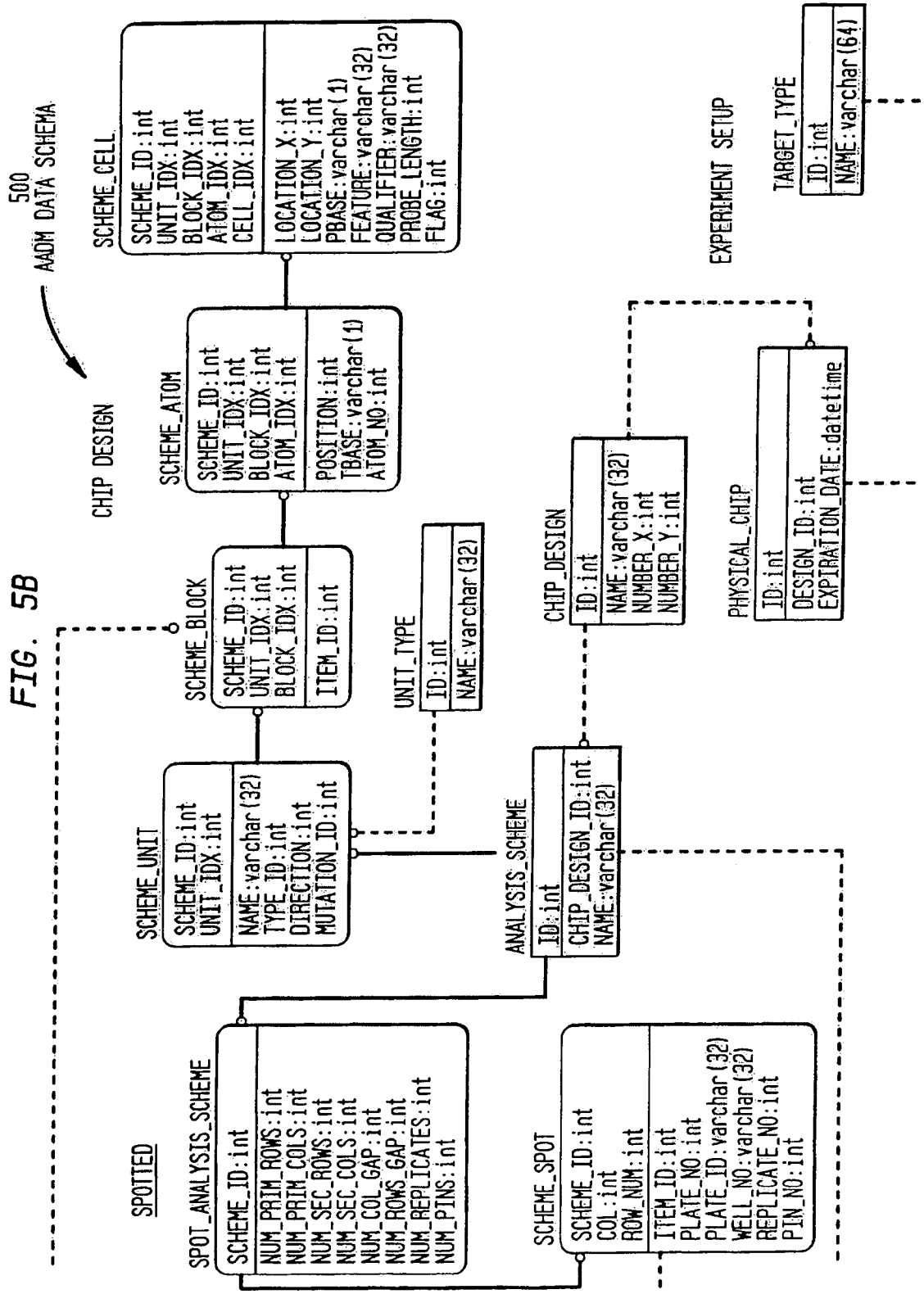
Figure 5C:
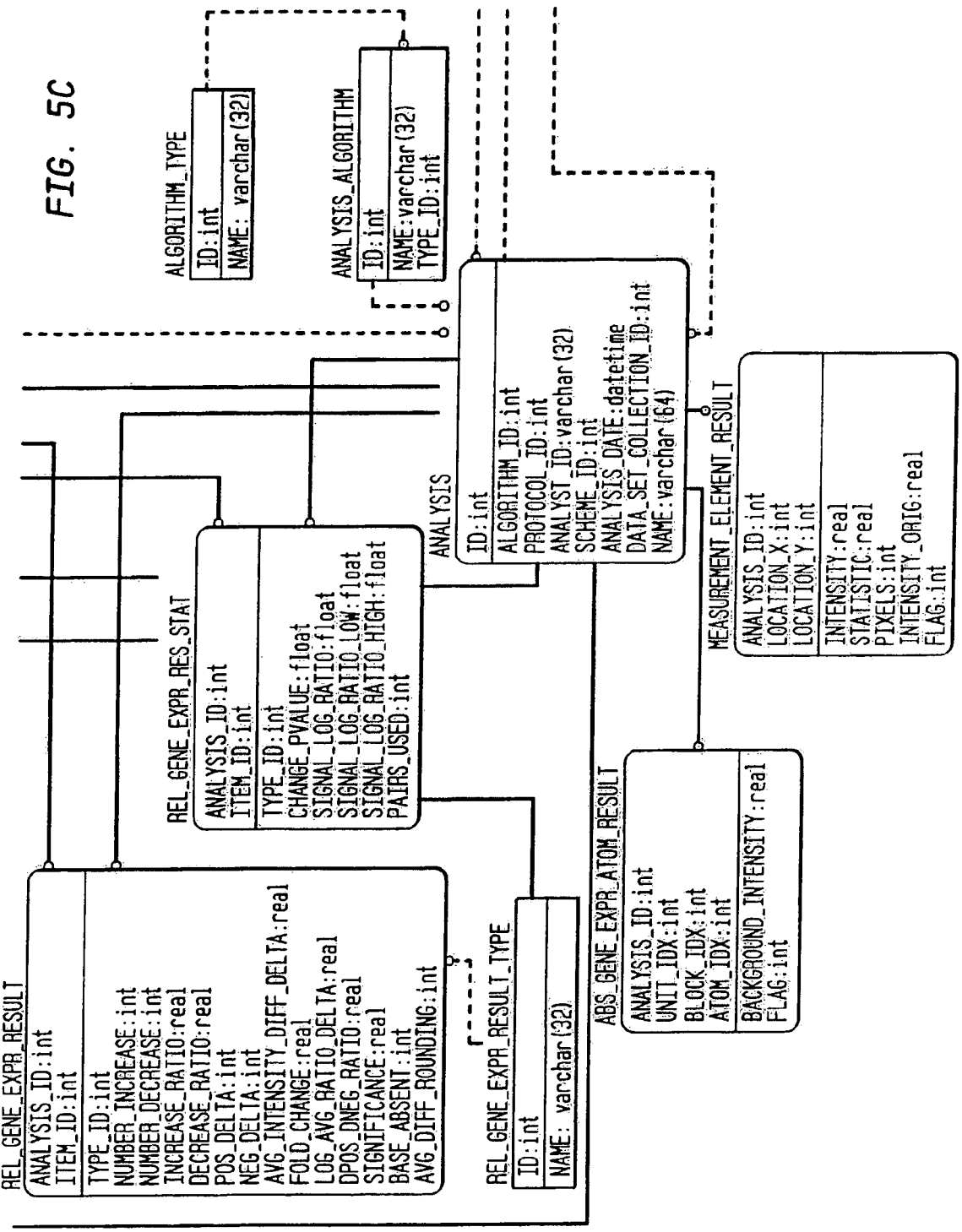
Figure 5D:
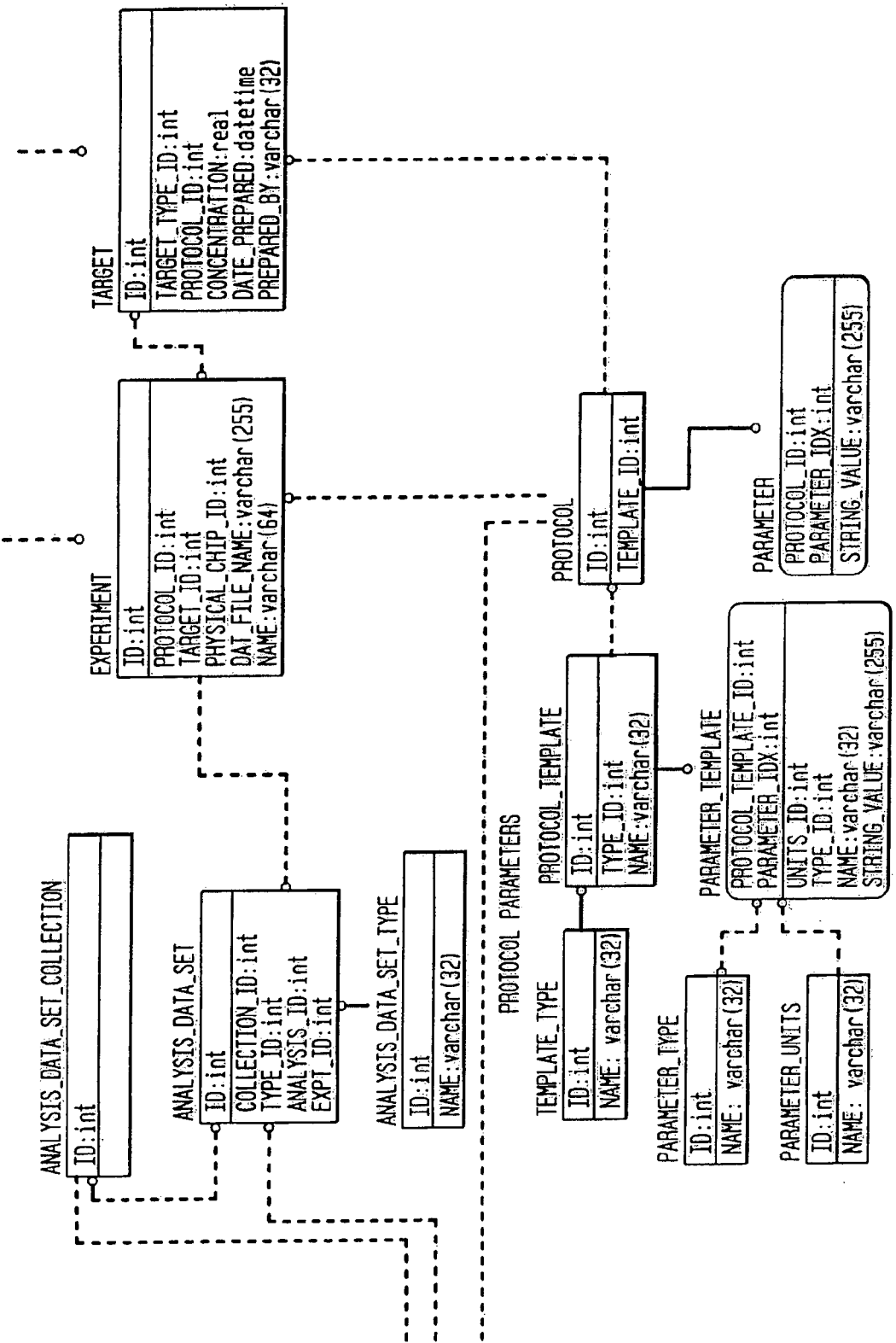

Workstations: Image data 276 may be stored and/or processed by a computer system such as any one or more of a number of workstations connected to network 125, generally and collectively referred to as workstations. In alternative implementations, image data 276 may be provided by workstations, via network 125, to LIMS server 120 where it may similarly be stored and/or processed. An example of workstations is workstation 130B, which is shown in FIG. 2 and, in greater detail, in FIG. 3. Workstation 130B may be any type of computer platform such as a workstation, a personal computer, a server, or any other present or future computer. Workstation 130B typically includes known components such as a processor 305, an operating system 310, a system memory 320, memory storage devices 325, system bus 304, and input-output controllers 330. Similarly, workstation 130A is illustrated in FIG. 4 comprising processor 405, an operating system 410, a system memory 420, memory storage devices 425, system bus 404, and input-output controllers 430. Each of these known devices is described below in greater detail with respect to corresponding devices of LIMS server 120. In particular, output controllers of input-output controllers 330 or 430 could include controllers for any of a variety of known display devices, network cards, and other devices well known to those of ordinary skill in the relevant art. If one of display devices 380 or 480 provides visual information, for example via a Graphical User Interface (GUI) 382 or 482, this information typically may be logically and/or physically organized as an array of pixels. Graphical user interface (GUI) controller 315 or 415 may comprise any of a variety of known or future software programs for providing graphical input and output interfaces to a user, such as experimenter 275, and for processing user inputs.

Image processing applications 399 may be any of a variety of known or future image processing applications. Examples of applications 399 are Affymetrix® Microarray Suite and Affymetrix® Jaguar™ software, noted above. Applications 399 may be loaded into system memory 320 and/or memory storage device 325 through one of input devices 302 or 402. Applications 399 as loaded into system memory 320 are shown in FIG. 3 as image processing applications executables 399A. In alternative implementations, applications 399 may be executed on LIMS server 120, or on one or more other computer platforms connected directly or indirectly (e.g., via another network, including the Internet or an intranet) to network 125.

In the illustrated embodiment, image data 276 is operated upon by executables 399A to generate intermediate results 390. Examples of intermediate results 390 are so-called cell intensity files (*.cel) and chip files (*.chp), and/or the data contained therein, generated by Affymetrix® Microarray Suite (as described, for example, in U.S. patent application Ser. Nos. 09/682,098, and 10/219,882, hereby incorporated herein by reference in their entireties for all purposes), and spot files (*.spt) generated by Affymetrix® Jaguar™ software (as described, for example, in PCT Application PCT/US 01/26390 and in U.S. patent application Ser. Nos. 09/681,819, 09/682,071, 09/682,074, and 09/682,076, all of which are hereby incorporated by reference herein in their entireties for all purposes). For convenience, the terms "file" or "data structure" may be used herein to refer to the organization of data, or the data itself generated or used by executables 399A and executable counterparts of other applications. However, it will be understood that any of a variety of alternative techniques known in the relevant art for storing, conveying, and/or manipulating data may be employed, and that the terms "file" and "data structure" therefore are to be interpreted broadly.

In one of the examples noted above, executables 399A receive image data 276 derived from a GeneChip® probe array and generates a cell intensity file. This file contains, for each probe scanned by scanner 270, a single value representative of the intensities of pixels measured by scanner 270 for that probe. Thus, this value is a measure of the abundance of tagged cRNA's present in the target that hybridized to the corresponding probe. Many such cRNA's may be present in each probe, as a probe on a GeneChip® probe array may include, for example, millions of oligonucleotides designed to detect the cRNA's. As noted, another file illustratively assumed to be generated by executables 399A is a chip file. In the present example, in which executables 399A include Affymetrix® Microarray Suite, the chip file is derived from analysis of the cell file combined in some cases with information derived from lab data 274 (described below) and library files (not shown) that specify details regarding the sequences and locations of probes and controls. The resulting data stored in the chip file includes degrees of hybridization, absolute and/or differential (over two or more experiments) expression, genotype comparisons, detection of polymorphisms and mutations, and other analytical results.

In another example, in which executables 399A includes Affymetrix® Jaguar™ software operating on image data from a spotted probe array, the resulting spot file includes the intensities of labeled targets that hybridized to probes in the array. Further details regarding cell files, chip files, and spot files are provided in U.S. Provisional Patent Application Nos. 09/682,098, and 09/682,071, incorporated by reference above. As will be appreciated by those skilled in the relevant art, the preceding and following descriptions of files generated by executables 399A are exemplary only, and the data described, and other data, may be processed, combined, arranged, and/or presented in many other ways.

Experimenter 275 and/or automated data input devices or programs (not shown) may provide data related to the design or conduct of experiments. As one further non-limiting example related to the processing of an Affymetrix® GeneChip® probe array, the experimenter may specify an Affymetrix catalogue or custom chip type (e.g., Human Genome U95Av2 chip) either by selecting from a predetermined list presented by MAS or by scanning a bar code related to a chip to read its type. MAS may associate the chip type with various scanning parameters stored in data tables including the area of the chip that is to be scanned, the location of chrome borders on the chip used for auto-focusing, the wavelength or intensity of laser light to be used in reading the chip, and so on. These other data are represented in FIGS. 2 and 3 as aspects of lab data 274. Data 274 may include, for example, the name of the experimenter, the dates on which various experiments were conducted, the equipment used, the types of fluorescent dyes used as labels, protocols followed, and numerous other attributes of experiments. As noted, executables 399A may apply some of this data in the generation of intermediate results 390. For example, information about the dyes may be incorporated into determinations of relative expression. Other (or all) aspects of lab data 274, such as the name of the experimenter, may be processed by executables 399A or may simply be preserved and stored in files or other data structures such as illustrative intermediate lab data 391. These aspects of lab data 274, together with intermediate results 390, are collectively shown as intermediate results and lab data 201 in FIGS. 2 and 3. FIG. 4 also presents data 201A, 201B, and 201C that may comprise data 201 associated with day 1, day 2, and day 3 respectively. Data 201 is provided, via network 125 of this example, to LIMS server 120.

LIMS Server 120: FIGS. 1 and 2 show a typical configuration of a server computer connected to a workstation computer via a network. For convenience, the server computer is referred to herein as LIMS server 120, although this computer may carry out a variety of functions in addition to those described below with respect to LIMS and LIMS-SDK software applications. Moreover, in some implementations any function ascribed to LIMS server 120 may be carried out by one or more other computers, and/or the functions may be performed in parallel by a group of computers. Network 125 may include a local area network, a wide area network, the Internet, another network, or any combination thereof.

An illustrative embodiment of LIMS server 120 is shown in greater detail in FIG. 2. Typically, LIMS server 120 is a network-server class of computer designed for servicing a number of workstations or other computer platforms over a network. However, server 120 may be any of a variety of types of general-purpose computers such as a personal computer, workstation, main frame computer, or other computer platform now or later developed. Server 120 typically includes known components such as a processor 205, an operating system 210, a system memory 220, memory storage devices 225, and input-output controllers 230. It will be understood by those skilled in the relevant art that there are many possible configurations of the components of server 120 and that some components that may typically be included are not shown, such as cache memory, a data backup unit, and many other devices. Similarly, many hardware and associated software or firmware components that may be implemented in a network server are not shown in FIG. 2. For example, components to implement one or more firewalls to protect data and applications, uninterruptable power supplies, LAN switches, web-server routing software, and many other components are not shown. Those of ordinary skill in the art will readily appreciate how these and other conventional components may be implemented.

Processor 205 may include multiple processors; e.g., multiple Intel Xeon® 700 MHz processors. As further examples, processor 205 may include one or more of a variety of other commercially available processors such as Pentium® processors from Intel, SPARC® processors made by Sun Microsystems, or other processors that are or will become available. Processor 205 executes operating system 210, which may be, for example, a Windows®-type operating system (such as Windows® 2000 with SP 1, Windows NT® 4.0 with SP6a) from the Microsoft Corporation; the Solaris operating system from Sun Microsystems, the Tru64 Unix from Compaq, other Unix® or Linux-type operating systems available from many vendors; another or a future operating system; or some combination thereof. Operating system 210 interfaces with firmware and hardware in a well-known manner, and facilitates processor 205 in coordinating and executing the functions of various computer programs that may be written in a variety of programming languages. Operating system 210, typically in cooperation with processor 205, coordinates and executes functions of the other components of server 120. Operating system 210 also provides scheduling, input-output control, file and data management, memory management, and communication control and related services, all in accordance with known techniques.

System memory 220 may be any of a variety of known or future memory storage devices. Examples include any commonly available random access memory (RAM), magnetic medium such as a resident hard disk or tape, an optical medium such as a read and write compact disc, or other memory storage device. Memory storage device 225 may be any of a variety of known or future devices, including a compact disk drive, a tape drive, a removable hard disk drive, or a diskette drive. Such types of memory storage device 225 typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory 220 and/or the program storage device used in conjunction with memory storage device 225. Also, data files or databases may be stored in system memory 220 such as, for example, intermediate results, lab data, and image data 201A; experiment and lab data in publish format 296; and process database 298.

In some embodiments, a computer program product is described comprising a computer usable medium having control logic (computer software program, including program code) stored therein. The control logic, when executed by processor 205, causes processor 205 to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 230 could include any of a variety of known devices for accepting and processing information from a user, whether a human or a machine, whether local or remote. Such devices include, for example, modem cards, network interface cards, sound cards, or other types of controllers for any of a variety of known input or output devices. In the illustrated embodiment, the functional elements of server 120 communicate with each other via system bus 204. Some of these communications may be accomplished in alternative embodiments using network or other types of remote communications.

As will be evident to those skilled in the relevant art, LIMS server application 280, as well as LIMS Objects 290 including LIMS servers 292 and LIMS API's 294 (described below), if implemented in software, may be loaded into system memory 220 and/or memory storage device 225 through one of input devices 202. LIMS server application 280 as loaded into system memory 220 is shown in FIG. 2 as LIMS server application executables 280A. Similarly, objects 290 are shown as LIMS server executables 292A and LIMS API object type libraries 294A after they have been loaded into system memory 220. All or portions of these loaded elements may also reside in a read-only memory or similar device of memory storage device 225, such devices not requiring that the elements first be loaded through input devices 202. It will be understood by those skilled in the relevant art that any of the loaded elements, or portions of them, may be loaded by processor 205 in a known manner into system memory 220, or cache memory (not shown), or both, as advantageous for execution.

LIMS Server Application 280: Details regarding the operations of illustrative implementations of application 280 are provided in U.S. patent application Ser. Nos. 09/682,098 (hereby incorporated by reference herein in its entirety for all purposes) and 60/220,587, incorporated by reference above. It will be understood that the particular LIMS implementation described in this patent application is illustrative only, and that many other implementations may be used with LIMS objects 290 and other aspects of the present or alternative embodiments.

Application 280, and other software applications referred to herein, may be implemented using Microsoft Visual C++ or any of a variety of other programming languages. For example, applications may also be written in Java, C++, Visual Basic, any other high-level or low-level programming language, or any combination thereof. As noted, certain implementations may be illustrated herein with respect to a particular, non-limiting, implementation of application 280, sometimes referred to as Affymetrix® LIMS. Full database functionality is intended to provide a data streaming solution and a single infrastructure to manage information from probe array experiments. Application 280 provides the functionality of database storage and retrieval system for accessing and manipulating all system data. A database server provides an automated and integrated data management environment for the end user. All process data, raw data and derived data may be stored as elements of the database, providing an alternative to a file-based storage mechanism. A database back end may also provide integration of application 280 into a customer's overall information system infrastructure. Data typically is accessible through standard interfaces and can be tracked, queried, archived, exported, imported and administered.

Application 280 of the illustrated implementation supports process tracking for a generic assay; adds enhanced administration functionality for managing synthesized probe arrays, spotted probe arrays, and data from these or other types of probe arrays that typically are published to a database schema standard such as Affymetrix' AADM standard; provides a full Oracle® database management software or SQL Server solution; supports publishing of genotype and sequence data; and provides a high level of security for the LIMS system.

In particular, application 280 of the illustrated example provides processes for enabling sample definition, experiment setup, hybridization, scanning, grid alignment, cell intensity analysis, probe array analysis, publishing, and a variety of other functions related to experimental design and implementation. Application 280 supports multiple experiments per sample definition via a re-queuing process, multiple hybridization and scan operations for a single experiment, data re-analysis, and publishing to more than one database. The process database, which may be implemented either as an Oracle or SQL Server database management system in the illustrated implementation, typically is supported by a COM communication layer to the process database. A gene-information database may also be provided to store chromosome and probe sequence information about the biological item on the probe array, and related information. Another feature, as noted, is publication of data in accordance with a database schema that typically is made public to enable third-party access and software interface development. For example, the AADM database schema, illustrated in FIG. 5, provides for publication of Affymetrix® GeneChip® data with support for either an Oracle or SQL server database management system. Among other structures, tables are provided in the AADM implementation that provide support for genotype data.

In particular implementations, a LIMS security database implements a role-based security level that is integrated with Windows NT® user authentication security. The security database supports role definition, functional access within a role, and assignment of NT groups and users to those roles. A role is a collection of users who have a common set of access rights to probe array data. In an illustrative implementation, roles may be defined per server/database, and a role member may be a member of multiple roles. The software determines a user's access rights based on predetermined rules governing such rights as a function of role or other variable. A function is a pre-determined action that is common to all roles. Each role is defined by the functions it can and cannot perform. Functions explicitly describe the type of action that a member of the role can perform. The functions supported by a newly created role include, but are not limited to, read process data, delete process data, update process data, archive process data, assume ownership of process data, import process data, export process data, delete AADM data, create a AADM database, and maintaining roles. When a new user is added to a role, they typically have access privileges for their data and read only access privilege for other user data within the same role. All non-role members are denied all access privileges to role member's data. When application 280 of the illustrated implementation is installed, at least two roles are created: administration and system user. The installer of the system software is added as a user to the administration role and a selected Windows NT® group is added as a user to the system user role.

In accordance with some implementations, a stand-alone application may be provided to enable user management capabilities. These capabilities include but are not limited to the following: AADM database creation, publish data deletion, process data deletion, taking ownership of process data, archiving and de-archiving of process data, data export, data import, role management, filter based find, managing expression analysis parameter sets, and managing sample and experiment attribution templates. Additionally, in accordance with the same or other implementations, the stand-alone application may provide an interface allowing data to be transferred between a database on the stand-alone application and a database on or managed by data servers. For example, the Affymetrix® GeneChip® Operating Software (GCOS) may be implemented on one or more workstations and may provide an AADM database and interface to one or more data servers that could include an Affymetrix® Array Information Management Server (AIMS) that contains one or more AADM databases. In the present example, GCOS may further provide an interface between the one or more workstations and the one or more data servers that could allow for the seamless transfer of data between databases. For example, data stored in the GCOS AADM database may be transferred to one or more AIMS server AADM databases using the GCOS interface. In the present example, the transfer does not require any format changes to the data providing for efficient transfer of data without loss of data integrity. Further details are provided in U.S. patent application Ser. No. 09/682,098, incorporated by reference above, and in U.S. Provisional Patent Application Ser. No. 60/442,684, hereby incorporated by reference herein in its entirety for all purposes.

LIMS Objects 290: In the illustrated implementation, LIMS Objects 290 is an object oriented programmers interface into LIMS server application 280. In the illustrated embodiment, LIMS objects 290 includes a number of Application Programmers Interfaces (APIs), generally and collectively represented as LIMS API's 294, and a number of LIMS servers, generally and collectively represented as LIMS servers 292. LIMS servers 292 may be distributed as out of process executables ("exe's") and LIMS API's 294 may be distributed as object type libraries ("tlb's"). Those of ordinary skill in the art will appreciate that various other distribution schemes and arrangements are possible in other implementations.

LIMS Objects 290 typically may be used by an application developer (represented in FIG. 2 by applications developer 200) who wishes to integrate in-house or third-party software systems with a LIMS such as LIMS server application 280. For example, it is illustratively assumed that applications developer 200 works in an enterprise that employs LIMS server application 280 to manage data related to experiments conducted on probe arrays, which may include any type of probe arrays such as GeneChip® probe arrays or spotted arrays (illustratively represented in FIG. 2 as hybridized probe arrays 272). It further is assumed for illustrative purposes that LIMS server application 280 is not a full-service system in that it does not provide functions such as laboratory process scheduling, sample management, instrument control, batch processing, and/or various data mining, processing, or visualization functions. Alternatively, application 280 may provide some or all of these functions, but applications developer 200 may wish to develop alternative or supplementary software applications to perform all or portions of any of these or other functions, and/or to integrate third-party software applications for these purposes. LIMS objects 290 provides developer 200 with tools to customize both the input of data into, and output of data from, LIMS server application 280.

LIMS objects 290 includes LIMS API's 294. API's 294, in the particular implementation of LIMS COM API's, includes the following classes: loading list of objects, reading an object, updating/writing an object, deleting an object, processing data, creating AADM-compliant databases, and invoking the analysis controller. API's are also included for objects, which are used by the previously listed classes.

Some implementations may include, as one of many possible examples of data schemes, a description of a database schema such as publish database schema description 278 of FIG. 2 or more particularly the AADM database schema described and illustrated in FIGS. 5A-5D as AADM data schema 500. This particular implementation may be divided for illustrative purposes into four sub-schemas: chip design, experiment setup, analysis results, and protocol parameters. The chip design sub-schema contains the overall chip description including the name, number of rows and columns of cells, the number of units, and a description of the units. The experiment setup sub-schema contains information on the chip used and the target that was applied. The analysis results sub-schema stores the results from expression analyses. The protocol parameters sub-schema contains parameter information relating to target preparation, experiment setup, and chip analysis. The AADM database can be queried for analysis results, protocol parameters, and experiment setup. Similar queries are enabled by Affymetrix® Data Mining Tool software, described in U.S. patent application Ser. No. 09/683,980, which is hereby incorporated herein by reference in its entireties for all purposes. The Affymetrix Data Mining Tool also uses a supplementary database called the Data Mining Info database, which stores user preferences, saved queries, frequently asked queries, and probe set lists. The Gene Info database, used by Affymetrix Microarray Suite, stores probe set information such as descriptions of probe sets, sequences that are tiled on an expression array, and user defined annotations. This database also stores lists of external database links that allow users to add links to internal/external databases, which could be public or private. The SPT, or "spot" file, contains the results of the image quantification and CSV information integrated together.

Additionally, a preferred embodiment may include other API's associated with LIMS objects 290 or alternatively implemented by an application produced by developer 200 such as user-provided applications (with API's) 450 illustrated in FIG. 4 as an element of image processing and/or user-provided applications 203 with image processing applications 399, and also stored in system memory 420 as user provided applications (with API's) executables 450A. Such API's may provide developer 200 with readable access to data elements contained in data files and/or data structures that, for instance, may allow developer 200 to import the data elements into applications 450. The API's used by applications 450 may be independently available from a variety of sources such as compact disk or other type of removable storage and/or as downloadable API's from one or more remote sources. As illustrated in FIG. 4, applications 450 may be implemented on a workstation such as workstations 130A. In some implementations, the API's may hide the format of the files from developer 200. In the presently described implementations the term "hide" generally refers to not showing the format to developer 200, as will be appreciated by those of ordinary skill in the related art, the format may not be otherwise altered in any way. The hidden format could eliminate the need for developer 200 to parse and maintain multiple versions of the files.

For example, one such set of API's may include the GeneChip® Data Access Components (GDAC) that provide programmatic access to data stored within the GeneChip® software systems. In addition to the API's included in GDAC additional elements may be included such as what those of ordinary skill in the related art refer to as COM interfaces and enumerant types. In the present example the GDAC API's may be further divided into three classifications that include GDAC-Files, GDAC-AADM, and GDAC-Exporter.

Continuing the example described above, GDAC-Files include a set of API's that provides developer 200 access to data stored in files generated by applications 399. Such files could include those generated by Affymetrix® Microarray Suite including .DAT (image data), .CEL (intensity data), .CHP (expression results data), .EXP (experiment data), and .CDF (probe array data) files. Accessible data for .CDF files may include probe set data; quality control data; probe array name; x, y coordinate data; and/or other probe array data. Any file having these general attributes, properties or functions may sometimes be referred to hereafter as a ".CDF-type file". Accessible data for .EXP files may include probe array type data; sample data; hybridization data; scan data; and/or other experiment data. Any file having these general attributes, properties or functions may sometimes be referred to hereafter as a ".EXP-type file". Accessible data for .DAT files may include scan data; corner feature data; intensity data by probe position; intensity data by line; and/or other image data. Any file having these general attributes, properties or functions may sometimes be referred to hereafter as a ".DAT-type file". Accessible data for .CEL files may include algorithm parameter data; probe intensity data by index; probe intensity data by position; probe intensity data by index and position; x, y coordinate position data; standard deviation data; pixel data, outlier data; masked feature data; background quality control data; and/or other intensity data. Any file having these general attributes, properties or functions may sometimes be referred to hereafter as a ".CEL-type file". Accessible data for .CHP files may include algorithm parameter data; header data; probe set data including data by index or all probe sets, statistical results, and empirical results; probe pair data including intensity by x, y coordinates, perfect match probes, mismatch probes, and background intensity; quality control data; and/or other expression results data. Any file having these general attributes, properties or functions may sometimes be referred to hereafter as a ".CHP-type file".

Also continuing the example described above, the GDAC-AADM provides developer 200 access to data stored using a data model such as the AADM data model previously described. Such access may include access to probe array design data including array type, rows, columns, probe sets names, probe pair data, and probe layout data; experimental data including probe array type, sample template and attribute data, and experiment template and attribute data; and/or analysis data including CEL intensities, CHP results, and/or parameter data.

Further continuing the example described above, GDAC-Exporter provides developer 200 the ability to export data from data files formatted by applications 399 or LIMS server 120 to one or more other types of formatted files that could, for instance, be a standardized format for probe array information such as what may be referred to as the MAGE-ML (Microarray Gene Expression-Markup Language) data exchange format. Additionally, GDAC-Exporter may export all data accessible by GDAC-Files and GDAC-AADM; LIMS or AIMS data; probe array data; sample data including templates and attributes; experiment data including templates and attributes; hybridization and scan environment data; and/or individual or multiple combinations of groups of EXP/DAT/CEL/CHP data. Additional examples of GDAC API's are provided in U.S. Provisional Patent Application Ser. Nos. 60/369,196, and 60/358,119, incorporated by reference above.

Figure 6:
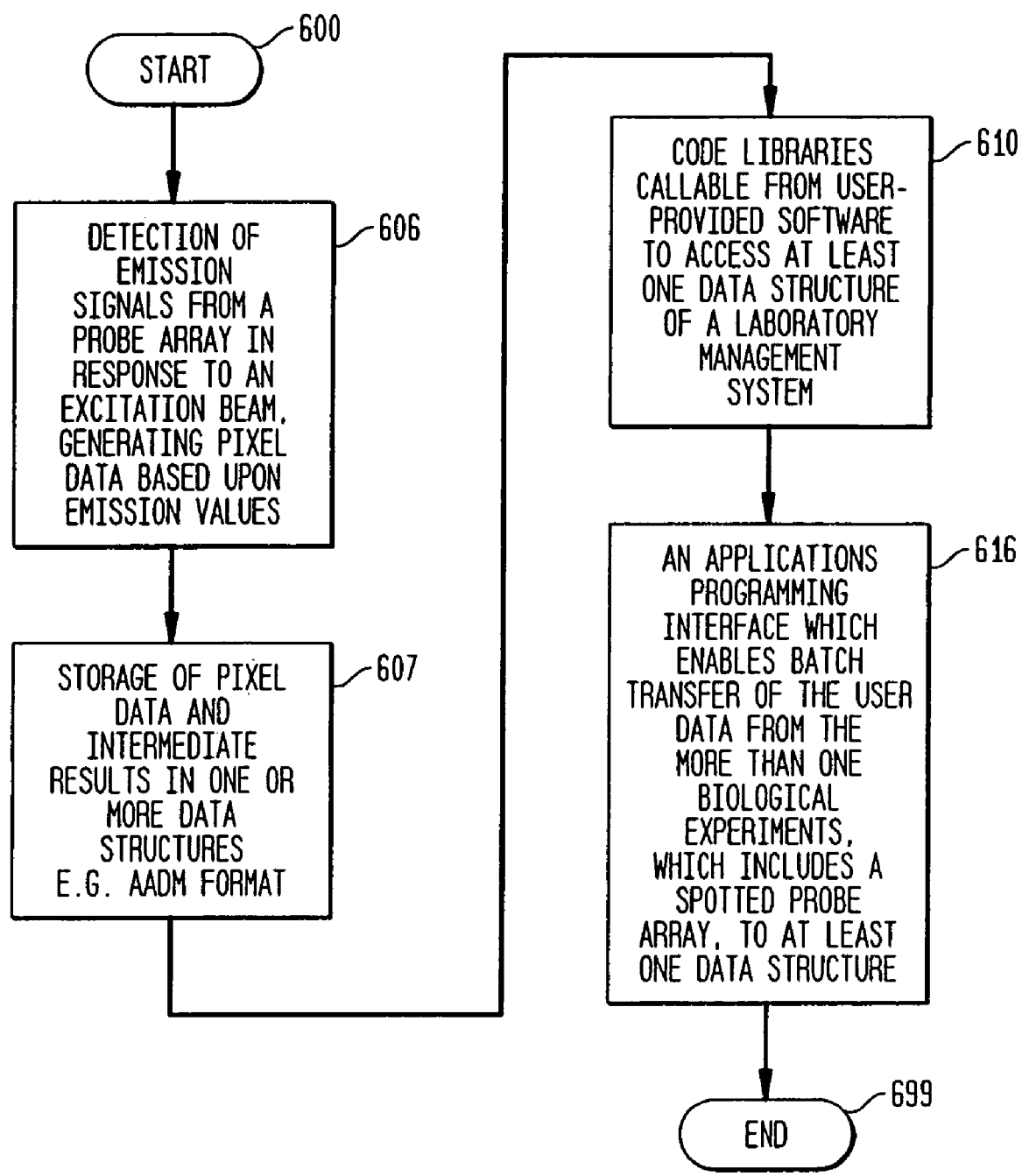
FIG. 6 is a flow chart of one embodiment of a method for implementing an API interface in a LIMS SDK application.

An illustrative example of a method of using the described API's is presented in FIG. 6 starting with step 600 and ending with step 699. Step 606 illustrates the step of scanner 270 detecting the emission signals from hybridized probe arrays 272. The detected emission signals may be processed by applications 399 resulting in intermediate results. Additionally, applications 399 may produce one or more types of results data files such as a .DAT file, .CEL file, or .CHP file. The intermediate results, detected emission signals, or other types of data elements or files may be stored in one or more data structures as illustrated in step 607. Alternatively, the results data files may be stored independently of a data structure as files on one or more workstations, servers, and local or remote data storage.

In a preferred embodiment the one or more data structures includes data structures contained in the AADM data model. Step 610 illustrates the step of accessing at least one data structure using an applications programming interface that include code libraries callable from user-provided application. Alternatively, developer 200 may use the code libraries to directly access data stored in at least one data structure or data file. The code libraries enable batch transfer of user data to at least one data structure as described in step 616. Alternatively, the code libraries allow access for developer 200 and/or for user-provided application to extract data elements from at least one data structure or data file without affecting the data content or integrity.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments. For example, some or all of the functions described as being carried out by workstation 130B could be carried out by server 120 and/or workstation 130A, or these functions could otherwise be distributed among these, other local and/or remote computer platforms.

Also, the functions of several elements may, in alternative embodiments, be carried out by fewer, or a single, element. Similarly, in some embodiments, any functional element may perform fewer, or different, operations than those described with respect to the illustrated embodiment. Also, functional elements shown as distinct for purposes of illustration may be incorporated within other functional elements in a particular implementation. Also, the sequencing of functions or portions of functions generally may be altered. Certain functional elements, files, data structures, and so on, may be described in the illustrated embodiments as located in system memory of a particular computer. In other embodiments, however, they may be located on, or distributed across, computer systems or other platforms that are co-located and/or remote from each other. For example, any one or more of data files or data structures described as co-located on and "local" to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures or files may be used and various described data structures or files may be combined or otherwise arranged. Numerous other embodiments, and modifications thereof, are contemplated as falling within the scope of the present invention as defined by appended claims and equivalents thereto.

What is claimed is:

1. An applications programming interface comprising:
   one or more code libraries that enable a developer of a user-provided application access to data stored in one or more file formats associated with a second application;
   wherein the one or more code libraries integrate the second application with the user-provided application; and
   wherein each of the file formats is organized to store data related to one or more biological probe arrays in one or more data files.

2. The applications programming interface of claim 1, wherein:
   the code libraries are callable from the user-provided application.

3. The applications programming interface of claim 1, wherein:
   the one or more code libraries are provided by a developer of the second application.

4. The applications programming interface of claim 1, wherein:
   the data related to the biological probe arrays comprises data selected from the group consisting of image data, intensity data, and results data.

5. The applications programming interface of claim 1, wherein:
   the data related to the biological probe arrays comprises data selected from the group consisting of experiment data, and probe array data.

6. The applications programming interface of claim 5, wherein:
   the data relate to the biological probe arrays comprise data that facilitates processing of intensity data representative of one or more target molecules hybridized to biological probes disposed upon one or more of the probe arrays.

7. The applications programming interface of claim 1, wherein:
   the user-provided application is unable to access the data stored in the one or more file formats without the one or more code libraries.

8. The applications programming interface of claim 1, wherein:
   the one or more data files are stored on one or more workstations or servers.

9. The applications programming interface of claim 8, wherein:
   the user-provided application is stored on the one or more workstations or servers.

10. The applications programming interface of claim 1, wherein:
    the user-provided application is stored remotely from the one or more workstations or servers.

11. The applications programming interface of claim 1, wherein:
    the one or more data files are stored in one or more remote storage devices.

12. The applications programming interface of claim 1, wherein:
    one or more code libraries further enable the developer of the user-provided application to organize the data in a standardized data exchange format.

13. The applications programming interface of claim 1, wherein:
    the standardized data exchange format is organized to exchange probe array data.

14. The applications programming interface of claim 1, wherein:
    the one or more code libraries hide the file formats from the developer.

15. The applications programming interface of claim 1, wherein:
    the one or more code libraries are integrated with the user-provided application.

16. A method for enabling access to one or more file formats organized to store data related to biological probe arrays comprising:
    enabling a developer of a user-provided application access to data stored in one or more file formats associated with a second application;
    wherein the one or more code libraries integrate the second application with the user-provided application; and
    wherein each of the file formats is organized to store data related to one or more biological probe arrays in one or more data files.

17. The method of claim 16, wherein:
    the code libraries are callable from the user-provided application.

18. The method of claim 16, wherein:
    the one or more code libraries are provided by a developer of the second application.

19. The method of claim 16, wherein:
    the data related to the biological probe arrays comprises data selected from the group consisting of image data, intensity data, and results data.

20. The method of claim 16, wherein:
    the data related to the biological probe arrays comprises data selected from the group consisting of experiment data, and probe array data.

21. The method of claim 20, wherein:
    the data related to the biological probe arrays comprise data that facilitates processing of intensity data representative of one or more target molecules hybridized to biological probes disposed upon one or more of the probe arrays.

22. The method of claim 16, wherein:
    the user-provided application is unable to access the data stored in the one or more file formats without the one or more code libraries.

23. The method of claim 16, wherein:
    the one or more data files are stored on one or more workstations or servers.

24. The method of claim 23, wherein:
the user-provided application is stored on the one or more workstations or servers.
25. The method of claim 16, wherein:
the user-provided application is stored remotely from the one or more workstations or servers.
26. The method of claim 16, wherein:
the one or more data files are stored in one or more remote storage devices.
27. The method of claim 16, wherein:
one or more code libraries further enable the developer of the user-provided application to organize the data in a standardized data exchange format.

28. The method of claim 16, wherein:
the standardized data exchange format is organized to exchange probe array data.
29. The method of claim 16, wherein:
the one or more code libraries hide the file formats from the developer.
30. The method of claim 16, wherein:
the one or more code libraries are integrated with the user-provided application.

* * * * *